(12) United States Patent
Park et al.

(10) Patent No.: US 9,089,271 B2
(45) Date of Patent: Jul. 28, 2015

(54) ACTUATION CONTROL SYSTEM OF A CAPSULE ENDOSCOPE

(75) Inventors: Suk Ho Park, Gwangju (KR); Jong Oh Park, Gyeonggi do (KR); Hyun Chul Choi, Jeollanam-do (KR); Kyung Rae Cha, Gwangju (KR); Se Mi Jeong, Jeollabuk-do (KR)

(73) Assignee: Industry Foundation of Chonnam National University, Gwangju (KR)

( * ) Notice: Subject to any disclaimer, the term of this patent is extended or adjusted under 35 U.S.C. 154(b) by 0 days.

(21) Appl. No.: 13/446,107

(22) Filed: Apr. 13, 2012

(65) Prior Publication Data

US 2013/0053640 A1     Feb. 28, 2013

(30) Foreign Application Priority Data

Aug. 31, 2011     (KR) .................. 10-2011-0087838

(51) Int. Cl.
*A61B 1/04*     (2006.01)
*A61B 1/00*     (2006.01)

(52) U.S. Cl.
CPC ............. *A61B 1/041* (2013.01); *A61B 1/00158* (2013.01)

(58) Field of Classification Search
CPC .......................... A61B 1/041; A61B 1/00158
USPC ........................ 600/103, 117, 118, 160, 178
See application file for complete search history.

(56) References Cited

U.S. PATENT DOCUMENTS

| 4,757,290 A * | 7/1988 | Keren ........................... 333/219 |
| 6,311,082 B1 | 10/2001 | Creighton, IV et al. |
| 2005/0052178 A1 | 3/2005 | Ries |
| 2010/0307517 A1 * | 12/2010 | Kawano et al. ............... 128/899 |

FOREIGN PATENT DOCUMENTS

| KR | 10-2011-0000779 A | 1/2011 |
| KR | 10-2011-0049842 A | 5/2011 |
| WO | WO 2006/092421 A1 | 9/2006 |

OTHER PUBLICATIONS

Choi et al., EMA system with gradient and uniform saddle coils for 3D locomotion of microrobot, Sensors and Actuators A 163 (2010) 410-417.*

* cited by examiner

Primary Examiner — Anhtuan T Nguyen
Assistant Examiner — Rynae Boler
(74) Attorney, Agent, or Firm — Rabin & Berdo P.C.

(57) ABSTRACT

A system for controlling actuation of a capsule endoscope includes a receiving unit receiving an image transmitted from the capsule endoscope; a coil unit generating a magnetic field for actuating the capsule endoscope by using current applied thereto; a power supply unit supplying power to the coil unit; and an actuation controller control the current applied to the coil unit and a coil rotational motor for adjusting of a posture and the location of the capsule endoscope based on the identified lesion or location of the capsule endoscope, wherein the coil unit includes a pair of Helmholtz coils and a pair of Maxwell coils that are fixedly disposed on a main axis; and a pair of uniform saddle coils and a pair of gradient saddle coils that are located inside the pair of the Helmholtz coils and the pair of the Maxwell coils to rotate around the main axis.

4 Claims, 8 Drawing Sheets

ACTUATION CONTROL SYSTEM OF A CAPSULE ENDOSCOPE

PRIORITY

This application claims the benefit under 35 U.S.C. §119 a of a Korean patent application filed in the Korean Intellectual Property Office on Aug. 31, 2011 and assigned Serial No. 10-2011-0087838, and the entire disclosure of which is hereby incorporated by reference.

BACKGROUND OF THE INVENTION

1. Field of the Invention

The present invention relates to an actuation control system of a capsule endoscope, and more particularly, to an actuation control system of a capsule endoscope, which is capable of precisely diagnosing not only a digestive system having a tubular shape such as an esophagus, a small intestine, or a large intestine but also a well of a wide organ such as a stomach and is capable of performing detailed examination of an organ at a desired location.

2. Description of the Related Art

A conventional flexible streamlined endoscope is inserted through a mouth or anus and controlled to perform an examination. To reduce difficulties in handling the endoscope and reduce a patient's suffering, a capsule endoscopic, which is swallowed through the mouth and passes through digestive systems for examination, is developed.

However, this capsule endoscope has a limited size so that various functions may not be performed. Also, because intestinal walls are slippery, the capsule endoscope is actuated in a passive manner such as peristalsis of the intestine.

To improve these disadvantages, a research on an actuation mechanism for actuating the capsule endoscope using an electromagnetic actuation system is conducted.

Meanwhile, in an electromagnetic actuation system for medical devices including the capsule endoscope, only a rotational motion and a straight line motion are enabled. Also, even if a translational motion is enabled, a coil system has a unsuitable coil structure in which a patient could not enter for treatment.

Meanwhile, numerous patent applications and patents, including U.S. Patent Publication No. 2008/0272873 (hereafter, "prior art document"), are related to a coil system for actuating the capsule endoscope.

As shown in FIG. 1, in the coil system for actuating the capsule endoscope disclosed in the prior art document, a total of 18 coils can be used to move the capsule endoscope in a certain direction.

However, the prior art coil system has a problem in that power consumption could be increased to move the capsule endoscope due to a high number of coils and each coil's role is not clearly defined.

SUMMARY OF THE INVENTION

Accordingly, the present invention has been made as a remedy of the above problems, and the present invention is to provide an actuation control system of a capsule endoscope that controls tilting and rotating motions as well as parallel and translational motions of the capsule endoscope, thereby being capable of precisely diagnosing not only a digestive system having a tubular shape such as an esophagus, a small intestine, or a large intestine but also a well of a wide organ such as a stomach and being capable of performing detailed examination of an organ at a desired location.

In one aspect of the present invention, a system for controlling actuation of a capsule endoscope includes a receiving unit configured to receive an image transmitted from the capsule endoscope; a coil unit configured to generate a magnetic field for actuating the capsule endoscope by using current applied thereto; a power supply unit configured to supply power to the coil unit; and an actuation controller configured to identify lesion or a location of the capsule endoscope based on the image received through the receiving unit and configured to control a motor for controlling the current applied to the coil unit and a posture and the location of the capsule endoscope based on the identified lesion or location of the capsule endoscope, wherein the coil unit comprises a pair of Helmholtz coils and a pair of Maxwell coils that are fixedly disposed on a main axis; and a pair of uniform saddle coils and a pair of gradient saddle coils that are located inside the pair of the Helmholtz coils and the pair of the Maxwell coils to rotate around the main axis.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION OF THE INVENTION

The features and advantages of the present invention will be more apparent from the following detailed description in view of the accompanying drawings. In the following description of the present invention, a detailed description of known functions and configurations incorporated herein will be omitted so as not to obscure the subject matter of the present invention.

The present invention now will be described more fully hereinafter with reference to the accompanying drawings.

Figure 1:
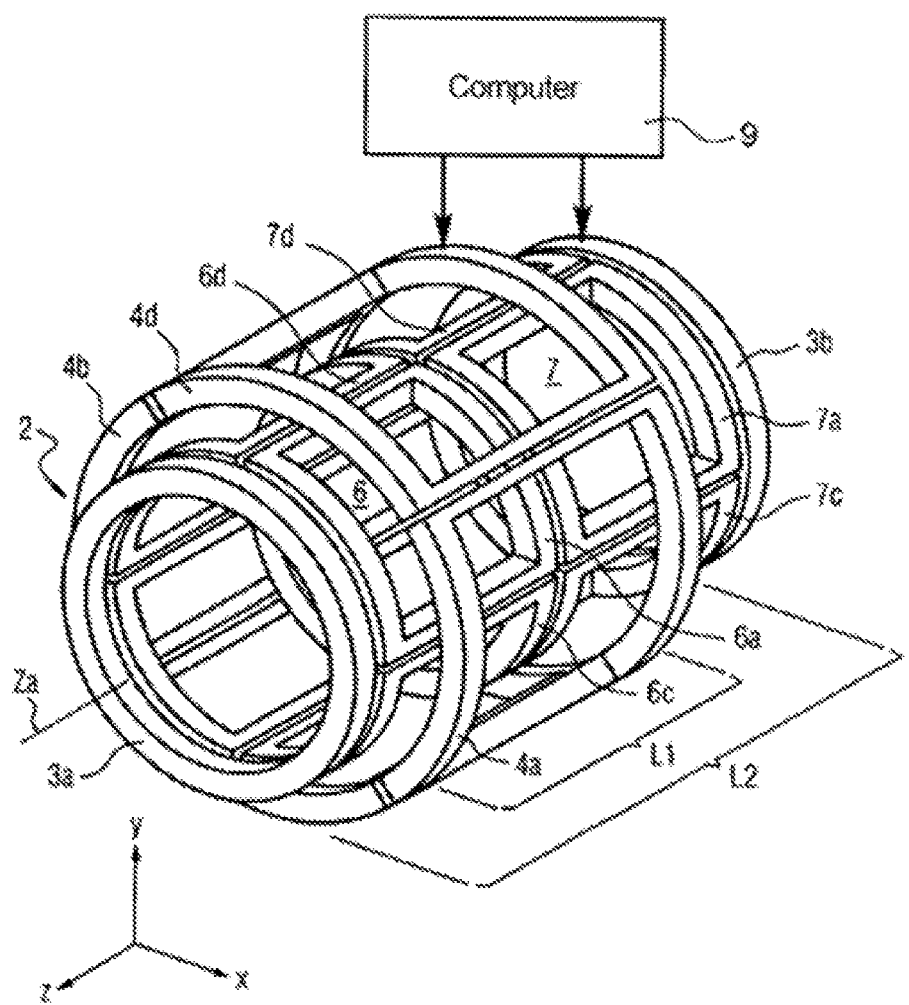
FIG. 1 is a configuration view illustrating a coil system for actuating a conventional capsule endoscope.
Figure 2:
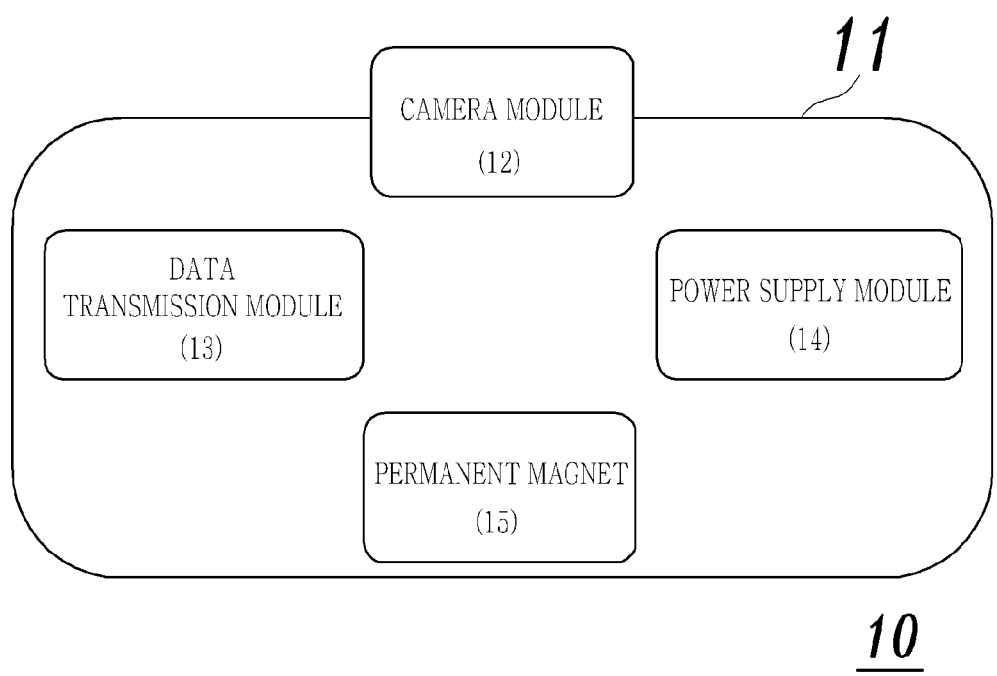
FIG. 2 is a view illustrating a configuration of a capsule endoscope according to the present invention.
Figure 8:
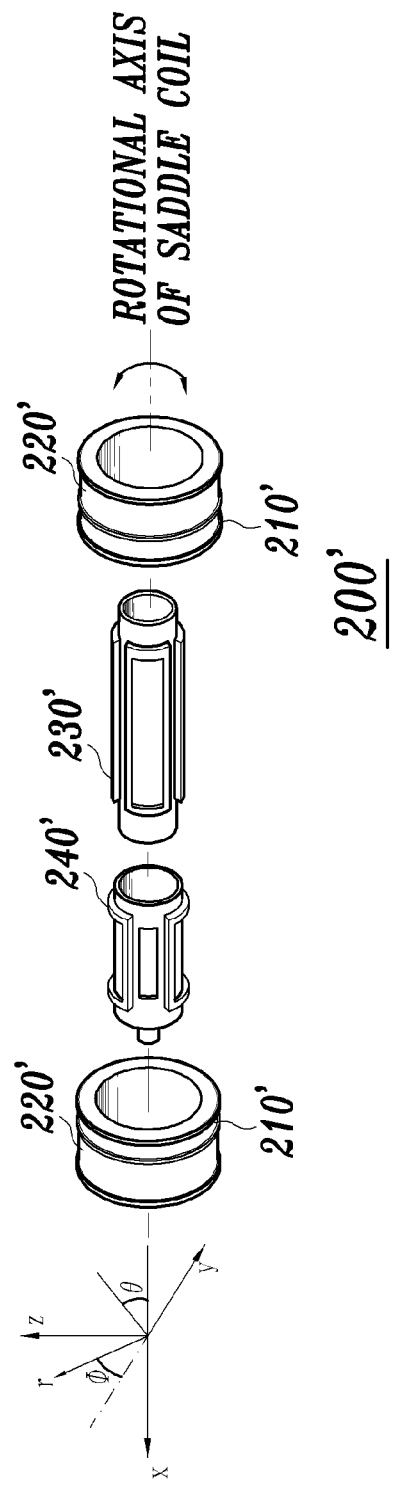
FIG. 8 is a view illustrating a configuration of a coil unit according to another exemplary embodiment of the present invention.

With reference to FIG. 2 or FIG. 8, an actuation control system of a capsule endoscope according to the present invention is described.

First, a capsule endoscope 10 that is driven by a capsule endoscope actuation control system (S) according to the present invention is described.

As shown in FIG. 2, the capsule endoscope 10 includes a capsule-shaped housing 11, a camera module 12, a data transmission module 13, a power supply module 14, and a permanent magnet 15 installed within the housing 11.

Specifically, the data transmission module 12 may be fixedly installed on a front or rear surface or a wall of the housing 11 along a longitudinal direction of the housing 11.

The data transmission module 13 transmits images obtained through the camera module 12 to outside.

The power supply module 14 supplies operational power to the camera module 12 and the data transmission module 13 and may use a battery.

The permanent magnet 15 may be magnetized in a certain direction within the housing 11 for electromagnetic actuation, and the capsule endoscope 10 may be driven by a magnetic field generated by an electromagnetic actuator coil.

Figure 3:
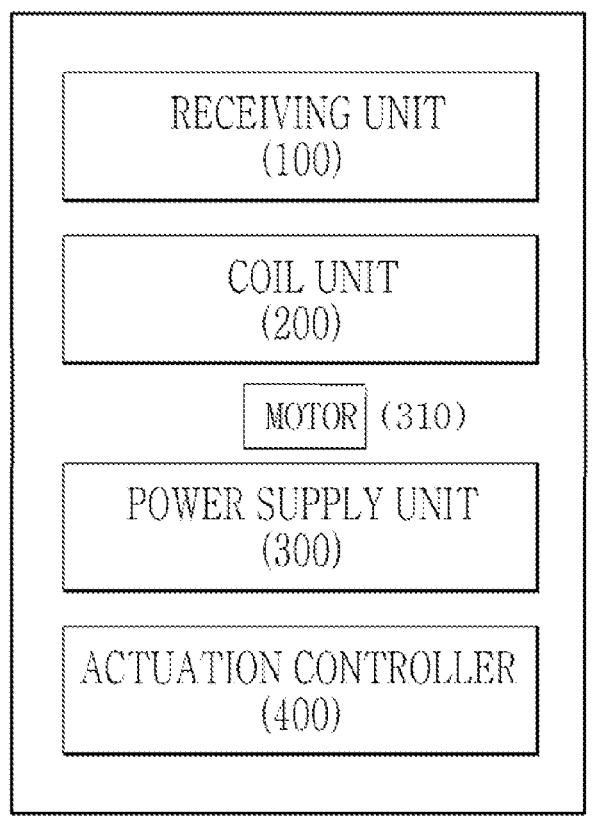
FIG. 3 is a view illustrating an entire configuration of a capsule endoscope actuating control system according to the present invention.

As shown in FIG. 3, the capsule endoscope actuation control system S includes a receiving unit 100, a coil unit 200, a power supply unit 300, and a actuation controller 400.

The receiving unit 100 receives images transmitted from the capsule endoscope 10.

The coil unit 200 generates a magnetic field for actuating the capsule endoscope 10 by using a current applied thereto.

Figure 4:
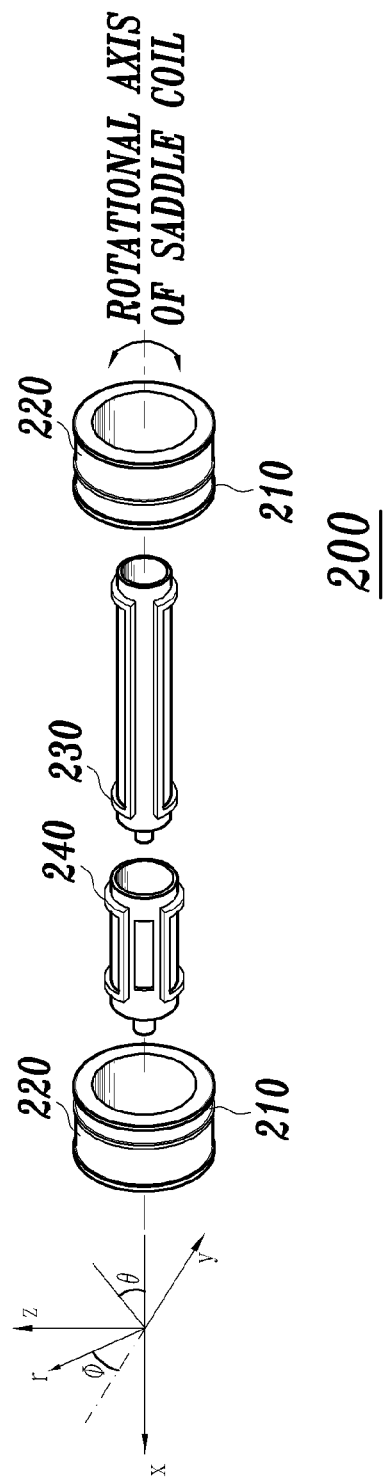
FIG. 4 is a view illustrating a configuration of a coil unit according to the present invention.

Specifically, as shown in FIG. 4, the coil unit 200 includes a pair of Helmholtz coils 210 and a pair of Maxwell coils 220 that are fixedly disposed on a main axis (or x axis) and a pair of uniform saddle coils 230 and a pair of gradient saddle coils 240 that are located inside the pair of the Helmholtz coils 210 and the pair of the Maxwell coils 220 to rotate around the main axis (or x axis).

The power supply unit 300 supplies power to the coil unit 200.

The actuation controller 400 identifies lesion or a location of the capsule endoscope 10 based on the images received through the receiving unit 100 and controls the currents to be applied to the coil unit 200 and a coil rotational motor (310) for adjusting of a posture and the location of the capsule endoscope 10.

Figure 5:
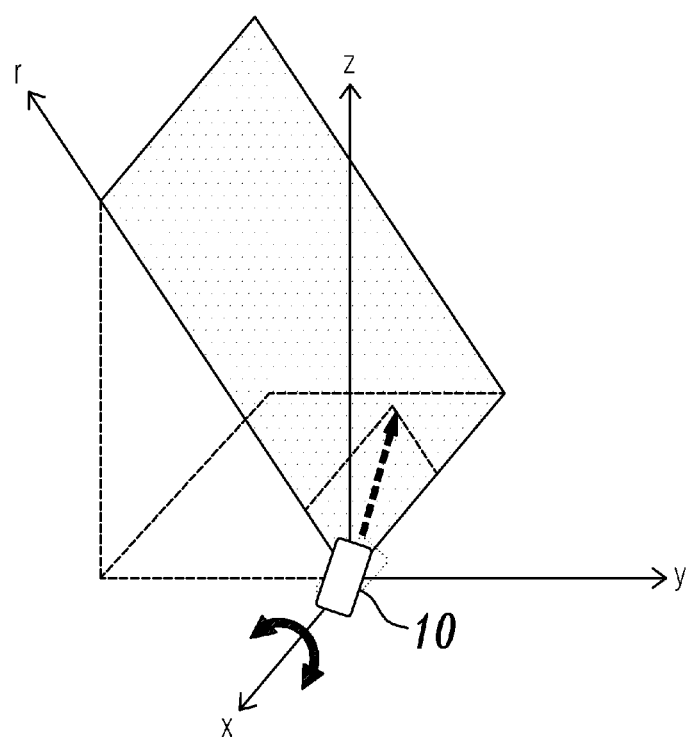
FIG. 5 is a view illustrating an exemplary embodiment of controlling a capsule endoscope to perform a tilting motion according to the present invention.

FIG. 5 is a view illustrating an exemplary embodiment of controlling the capsule endoscope 10 to perform a tilting motion according to the present invention As shown in FIG. 5, in order for the capsule endoscope 10 to perform a tilting motion in a certain direction on a plane (or an x-r plane) that is tilted at a certain angle relative to the x axis, the actuation controller 400 adjusts strength of magnetic fields of the pair of the Helmholtz coils 210 and the pair of the uniform saddle coils 230 while the pair of the uniform saddle coils 230 and the pair of the gradient saddle coils 240 coincide with an r axis, thereby realizing the tilting motion of the capsule endoscope 10 at a certain angle.

Figure 6:
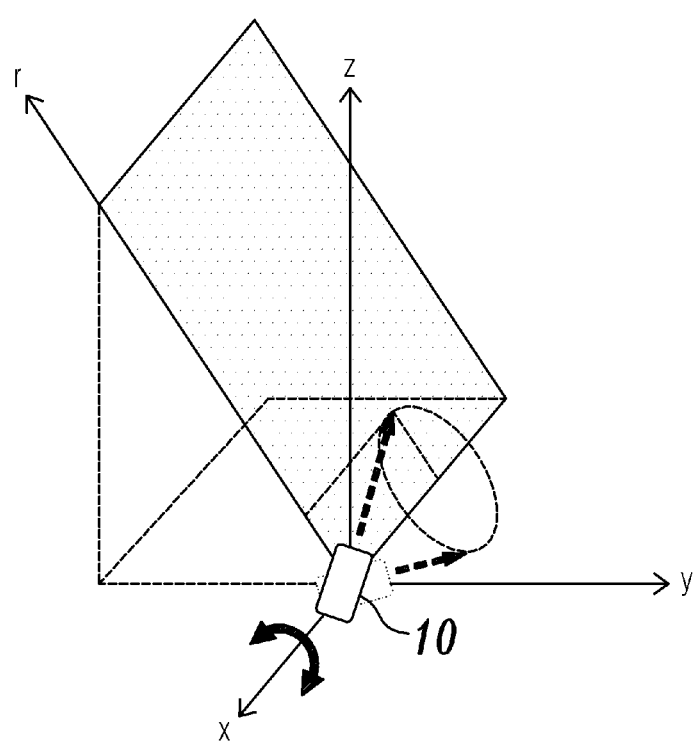
FIG. 6 is a view illustrating an exemplary embodiment of controlling a capsule endoscope to rotate around a certain axis according to the present invention.

FIG. 6 is a view illustrating an exemplary embodiment of controlling the capsule endoscope 10 to rotate around a certain axis according to the present invention.

As shown in FIG. 6, in order for the capsule endoscope 10 to rotate around a certain axis on the plane (or the x-r plane) that is tilted at a certain angle relative to the x axis, the actuation controller 400 adjusts strength of magnetic fields generated by the pair of the Helmholtz coils 210 and the pair of the uniform saddle coils 230 and rotation the generated magnetic fields while the pair of the uniform saddle coils 230 and the pair of the gradient saddle coils 240 coincide with the r axis, thereby realizing a rotational motion of the capsule endoscope 10 around a certain axis.

Figure 7:
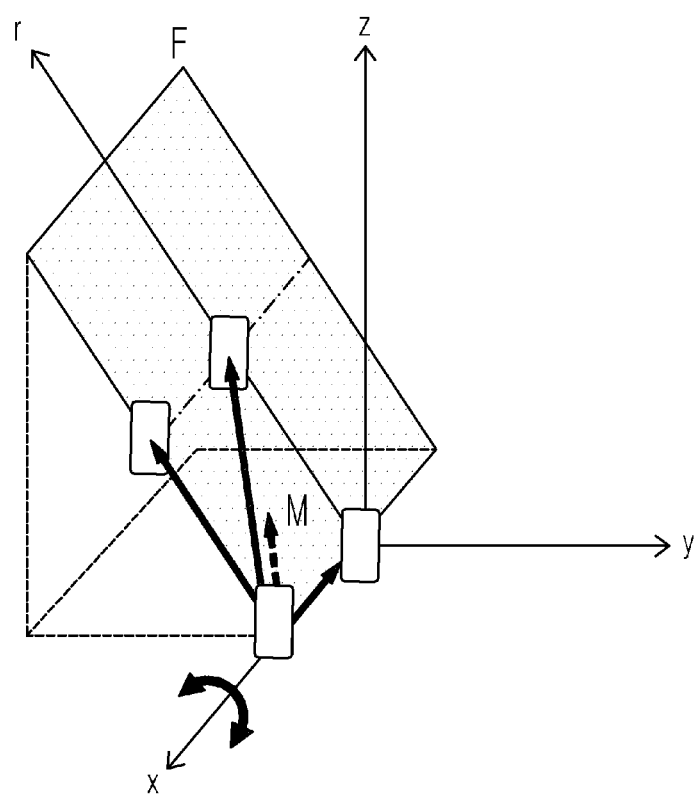
FIG. 7 is a view illustrating an exemplary embodiment of controlling a capsule endoscope to perform a parallel motion and a translational motion according to the present invention.

FIG. 7 is a view illustrating an exemplary embodiment of controlling the capsule endoscope 10 to perform a parallel motion and a translational motion according to the present invention.

As shown in FIG. 7, in order for the capsule endoscope 10 to perform a parallel motion and a translational motion on the plane (or the x-r plane) that is tilted at a certain angle relative to the x axis, the actuation controller 400 adjusts strength of the magnetic fields of the pair of the Helmholtz coils 210 and the pair of the uniform saddle coils 230 to be aligned in a certain direction while the pair of the uniform saddle coils 230 and the pair of the gradient saddle coils 240 coincide with the r axis. Accordingly, a gradient of the magnetic fields generated by the pair of the Maxwell coils 220 and the pair of the gradient saddle coils 240 is adjusted, thereby generating a driving force of the capsule endoscope 10 in a desired direction.

FIG. 8 is a view illustrating a configuration of a coil unit 200' according to another exemplary embodiment of the present invention. As shown in FIG. 8, the coil unit 200' includes a pair of Helmholtz coils 210' and a pair of Maxwell coils 220' that are fixedly disposed on a main axis (or x axis) and two pairs of uniform saddle coils 230' and a pair of gradient saddle coils 240' that are located inside the pair of the Helmholtz coils 210' and the pair of the Maxwell coils 220', wherein the two pairs of the uniform saddle coils 230' are placed on a plane that is perpendicular to the main axis (or x axis), the two pairs of the uniform saddle coils 230' being fixedly disposed on the plane to be perpendicular to each other, and the pair of the gradient saddle coils 240' are disposed to rotate around the main axis (x axis).

A method of controlling the capsule endoscope 10 to realize the tilting motion by using the capsule endoscope actuation control system S including the coil unit 200' according to another exemplary embodiment of the present invention is described.

In order for the capsule endoscope 10 to realize a tilting motion in a certain direction on a plane (or the x-r plane) that is tilted at a certain angle relative to the x axis, the actuation controller 400 adjusts strength and direction of magnetic fields of the pair of the Helmholtz coils 210' and the two pairs of the uniform saddle coils 230', thereby realizing the tilting motion of the capsule endoscope 10 at a certain angle.

Also, a method of controlling the capsule endoscope 10 to rotate around a certain axis by using the capsule endoscope actuation control system S including the coil unit 200' according to another exemplary embodiment of the present invention is described.

In order for the capsule endoscope 10 to rotate around a certain axis on the plane (or the x-r plane) that is tilted at a certain angle relative to the x axis, the actuation controller 400 adjusts strength and direction of the magnetic fields generated by the pair of the Helmholtz coils 210' and the two pairs of the uniform saddle coils 230', thereby realizing a rotational motion of the capsule endoscope 10 around a certain axis.

Further, a method of controlling the capsule endoscope 10 to realize a parallel motion and a translational motion by using the capsule endoscope actuation control system S including the coil unit 200' according to another exemplary embodiment of the present invention is described.

In order for the capsule endoscope 10 to realize the parallel motion or the translational motion on the plane (or the x-r plane) that is tilted at a certain angle relative to the x axis, the actuation controller 400 adjusts strength and direction of the magnetic fields of the pair of the Helmholtz coils 210' and the two pairs of the uniform saddle coils 230' while the pair of the gradient saddle coils 240' coincide with the r axis to be aligned in a certain direction. Accordingly, a gradient of the magnetic fields generated by the pair of the Maxwell coils 220' and the pair of the gradient saddle coils 240' is adjusted, thereby generating a driving force of the capsule endoscope 10 in a desired direction.

According to the present invention described above, tilting and rotating motions as well as parallel and translational motions of the capsule endoscope can be controlled so that the present invention can apply not only to the capsule endoscope capable of observing digestive systems such as esophagus, small intestine, or large intestine, but also to various medical fields for minimally invasive surgery such as a micro robot capable of moving inside blood vessels to treat disease or a micro robot capable of moving inside a spinal canal.

In the above, although the embodiments of the present invention have been described with reference to the accompanying drawings, a person skilled in the art should apprehend that the present invention can be embodied in other specific forms without departing from the technical spirit or essential characteristics thereof. Thus, the embodiments described above should be construed as exemplary in every aspect and not limiting.

What is claimed is:

1. A system for controlling actuation of a capsule endoscope, the system comprising:
    a receiving unit receiving images transmitted from the capsule endoscope;
    a coil unit generating a magnetic field for actuating the capsule endoscope by using applied current thereto;
    a power supply unit supplying power to the coil unit; and
    an actuation controller identifying lesion or a location of the capsule endoscope based on the images received through the receiving unit and controlling a motor for controlling the current applied to the coil unit and a posture and the location of the capsule endoscope based on the identified lesion or location of the capsule endoscope,
    wherein the coil unit comprises
    a pair of Helmholtz coils fixedly disposed on a main axis,
    a pair of Maxwell coils fixedly disposed on the main axis,
    two pairs of uniform saddle coils located inside the pair of the Helmholtz coils and the pair of the Maxwell coils and fixedly disposed on a plane perpendicular to the main axis, the two pairs of the uniform saddle coils being disposed to be orthogonal to each other and not rotating about the main axis, and
    a pair of gradient saddle coils disposed inside the pair of the Helmholtz coils and the pair of the Maxwell coils and rotating about the main axis.

2. The system according to claim 1, wherein the actuation controller adjusts strength and a direction of magnetic fields of the pair of the Helmholtz coils and the two pairs of the uniform saddle coils such that the capsule endoscope performs a tilting motion at a certain angle.

3. The system according to claim 1, wherein the actuation controller adjusts strength and a direction of magnetic fields generated by the pair of the Helmholtz coils and the two pairs of the uniform saddle coils such that the capsule endoscope performs a rotational motion around a certain axis.

4. The system according to claim 1, wherein the actuation controller adjusts strength and a direction of magnetic fields of the pair of the Helmholtz coils and the two pairs of the uniform saddle coils to be aligned in a certain direction while the pair of the gradient saddle coils coincide with an r axis, such that a gradient of magnetic fields generated by the pair of the Maxwell coils and the pair of the gradient saddle coils are adjusted to generate a driving force of the capsule endoscope in a desired direction.

* * * * *